United States Patent [19]

Park et al.

[11] Patent Number: 5,286,498

[45] Date of Patent: Feb. 15, 1994

[54] RAPID EXTRACTION OF CIGUATOXIN FROM CONTAMINATED TISSUES

[75] Inventors: Douglas L. Park; Pedro M. Gamboa, Both of Tucson, Ariz.

[73] Assignee: Hawaii Chemtect Incorporated, Pasadena, Calif.

[21] Appl. No.: 878,707

[22] Filed: May 1, 1992

[51] Int. Cl.$^5$ .................. A61K 35/12; A61K 31/195; C07H 15/00

[52] U.S. Cl. .................................. 424/520; 514/561; 536/18.5; 435/7.21

[58] Field of Search ...................... 424/520; 435/7.21; 536/18.5, 18.7, 22.1; 514/561

[56] References Cited

U.S. PATENT DOCUMENTS 4,816,392 3/1989 Hokama .................................. 435/7

OTHER PUBLICATIONS

Y. Hokama et al., "Evaluation of the Stick Enzyme Immunoassay in *Caranx* sp. and *Seriola dumerili* Associated With Ciguatera,", *J. Clin. Lab. Anal.*, 4, 363–366 (1990).

Hokama et al., "Monoclonal Antibodies in the Detection of Ciguatoxin and Other Toxic Polyethers in Fish Tissues by a Rapid Poke Stick Test," Proceedings of the 5th Int'l. Coral Reef Congress, Tahiti, vol. 4 (1985).

Hokama et al., "A Radioimmunoassay for the Detection of Ciguatoxin," *Toxicon*, 15, 317–325 (1977).

Hokama et al., "A Rapid Enzyme-Immunoassay for the Detection of Ciguatoxin in Contaminated Fish Tissues,"*Toxicon*, 21, 817–824 (1983).

Hokama, "A Rapid, Simplified Enzyme Immunoassay Stick Test for the Detection of Ciguatoxin and Related Polyethers from Fish Tissues," *Toxicon*, 23, 939–946 (1985).

Hokama et al., "Assessment of a Rapid Enzyme Immunoassay Stick Test for the Detection of Ciguatoxin and Related Polyether Toxins in Fish Tissues," *Biol. Bull.*, 172, 144–153 (1987).

Hokama, "Ciguatera Fish Poisoning," *J. Clin. Lab. Anal.*, 2, 44–50 (1988).

Hokama et al., "Monoclonal Antibody (MAb) in Detection of Ciguatoxin (CTX) and Related Polyethers by the Stick-Enzyme Immunoassay (S-EIA) in Fish Tissues Associated with Ciguatera Poisoning," presented at the 7th Int'l. IUPAC Symposium on Mycotoxins and Phycotoxins, Tokyo, Japan, 16–19 Aug. 1988.

Hokama, "Simplified Solid-Phase Immunobead Assay for Detection of Ciguatoxin and Related Polyethers," *J. Clin. Lab. Anal.*, 4, 213–217 (1990).

McMillan et al., "Ciguatera Fish Poisoning in the United States Virgin Islands: Preliminary Studies," *J. Coll. Virgin Islands*, 6, 84–107 (1980).

Kimura et al., "Evaluation of the radioimmunoassay (RIA) for detection of Ciguatoxin (CTX) in fish tissues," *J. Fish Biol.*, 21, 671–680 (1982).

Scheur et al., Science 155: 1267–1268, 1967.

*Primary Examiner*—John W. Rollins
*Attorney, Agent, or Firm*—Christie, Parker & Hale

[57] ABSTRACT

The present invention relates to methods for the rapid extraction of ciguatoxins from tissue samples. In one embodiment, a tissue sample is extracted with a first solvent to solubilize and extract ciguatoxin from the sample. A second solvent, which is not soluble in the first solvent and which extracts contaminants but not ciguatoxin, is then added. The phases formed by the first and second solvents are separated, and the first solvent phase is collected. The first solvent is evaporated from the first solvent phase to produce a residue which is resuspended in a third solvent. A fourth solvent, which is not soluble in the third solvent and which extracts contaminants but not ciguatoxin, is added to the third solvent/residue mixture. The phases formed by the third and fourth solvents are separated, and the third solvent phase, which comprises ciguatoxin, is collected. In a second embodiment, a sample is applied to a coupled antibody-resin. The coupled antibody-resin is washed with a solution to remove unbound material, but not ciguatoxin, from the coupled antibody-resin, and ciguatoxin is then eluted from the coupled antibody-resin.

11 Claims, No Drawings

RAPID EXTRACTION OF CIGUATOXIN FROM CONTAMINATED TISSUES

FIELD OF THE INVENTION

The present invention relates to methods for rapidly extracting ciguatoxin from serum or other samples containing ciguatoxin.

BACKGROUND OF THE INVENTION

Ciguatera poisoning is a particular type of fish poisoning which results from the ingestion of contaminated fish. Intoxication is associated with the consumption of toxins produced by tropical dinoflagellates, including *Gambierdiscus toxicus*, which are subsequently passed along the food chain to man. Ciguatoxins are polyether marine toxins, and approximately 27 different ciguatoxins are known, approximately 23 of which are toxic to man. Ciguatera toxins are odorless, tasteless, heat-stable, and generally undetectable by simple chemical tests.

Humans are susceptible to ciguatera poisoning, both from eating toxic herbivores which ingest the dinoflagellates while feeding on red or brown algae, and from eating carnivores which have eaten the toxic herbivores. An accurate assessment of the incidence of ciguatera poisoning is not available; however, it is estimated that, each year, from 10,000 to 50,000 people who live in or visit tropical and subtropical areas suffer from ciguatera poisoning. Additionally, the threat of this contamination results in enormous economic losses in the recreational and commercial exploitation of fishery resources in the affected areas.

Ciguatera poisoning is considered a world health problem. The illness is prevalent in the tropical Caribbean and subtropical North Atlantic, as well as the Pacific regions. Although, in the past, toxic outbreaks were limited to the endemic areas, interregional transport of fish can result in outbreaks in nontropical parts of the world.

Ciguatera poisoning outbreaks have been documented in Canada, Egypt, Sri Lanka, Italy, Japan, Venezuela, French Polynesia, French Antilles, and Australia. In the United States, cases have been reported in Florida, Louisiana, Texas, Kansas, Hawaii, Samoa, the Virgin Islands, Massachusetts, Puerto Rico, New York, Tennessee, and Washington, D.C. A few cases of ciguatera poisoning were reported in Vermont after several restaurants served toxic barracuda imported from tropical regions.

The onset of the clinical symptoms of ciguatera poisoning occurs within 10 minutes to 24 hours following the consumption of contaminated fish. Ciguatera poisoning affects the digestive system (resulting in abdominal pain, diarrhea, vomiting, nausea); the cardiovascular system (resulting in bradycardia, hypotension, tachycardia); and the neurological system (resulting primarily in paresthesia and dysesthesia).

The symptoms vary in severity depending on the patient, with the reported mortality rate being as high as 12% in some outbreaks, and about one per 1,000 cases in other outbreaks. Death is usually due to respiratory paralysis. Postmortem examination shows acute visceral congestion with occasional hemorrhages.

The incubation periods and symptoms are highly variable, even among persons who have consumed the same fish. Some individuals do not experience symptoms at all, while others are seriously affected. For most patients, the first signs to appear are paresthesia and numbness around the lips and tongue, and numbness or tingling of the extremities. For some patients, the earliest manifestations are diarrhea and vomiting. These abdominal symptoms are usually resolved within days. The neurological symptoms persist for weeks or months in some individuals.

The presence of paresthesia is considered to differentiate ciguatera poisoning from other forms of non-seafood poisoning or mild gastroenteritis, but this symptom also occurs in paralytic shellfish poisoning, neurotoxic shellfish poisoning, and diarrheic shellfish poisoning. Ciguatera poisoning is differentiated by recent dietary history, and perhaps the only hallmark symptom is the reversal of temperature perception. However, this symptom has also been documented for neurotoxic shellfish poisoning.

In general, the neural symptoms last for about six weeks, but some patients still have problems after months or even years. The long-term symptoms usually include loss of energy, arthralgia (especially of the knees, ankles, shoulders, and elbows), myalgia, headache, and pruritus. Characteristically, the symptoms fluctuate, sometimes with a pseudo-diurnal periodicity. Not infrequently, the symptoms may return during periods of stress, illness, or malnutrition.

An initial intoxication does not confer immunity. On the contrary, reports of sensitization to the toxin are common. After eating fish that does not produce symptoms in others, patients who have previously suffered from ciguatera poisoning experience recurrences of typical ciguatera poisoning symptoms. The effects of the toxin appear to be dose-related. Recurrent or multiple attacks of ciguatera poisoning result in a clinically-more-severe illness compared to that of patients experiencing the disease for the first time.

There is no curative treatment presently known for ciguatera poisoning. Traditionally, the immediate first-aid treatment is to induce vomiting, to try to eliminate the toxin(s). This is of little help, however, because the existence of the illness is not suspected until the initial symptoms have appeared (which is usually long after the toxin-containing fish have been digested).

Successful treatment has been carried out by thoroughly cleansing the gastrointestinal (GI) track with enemas and magnesium citrate saline catharsis, then instituting a strict diet containing no fish, shellfish, or their byproducts, no nuts, and no alcohol.

In the Marshall Islands, 24 patients with acute ciguatera poisoning were treated with intravenous mannitol, and each patient's condition improved dramatically. All neurological and muscular dysfunctions in these patients exhibited marked reduction within minutes, but gastrointestinal symptoms disappeared more slowly. In Australia, 12 patients received mannitol therapy, also resulting in significant improvement. A recommended treatment of 1.0 g of mannitol/kg is expected to benefit acutely intoxicated victims. The mechanism of action of this treatment is not fully understood. However, it is inexpensive and apparently safe, and has therefore been considered for treating patients experiencing significant ciguatera illness.

Currently, no other treatments for ciguatera poisoning are available, and even available treatments are only effective after an accurate diagnosis has been made. Since the symptoms associated with ciguatera poisoning vary with the individual, and often mimic other types of poisoning, chemical and animal testing have been essential to arrive at an accurate diagnosis.

Immunological methods, such as those described in U.S. Pat. No. 4,816,392, have been developed for the identification of ciguatoxin in fish, and similar immunological methods have also been applied to testing serum taken from persons suspected of suffering from ciguatera poisoning. However, these testing methods are qualitative, in that they give a "plus-minus" result, and may not accurately indicate the concentration of the toxin detected. Due to the individual differences in the doses required to cause symptoms, the level of ciguatoxin in the blood of such patients may be very low. Therefore, if a patient is very sensitive to ciguatoxin, the amount of circulating toxin may be below the limits of detection for the testing methods available, and, as a result, the condition may not be accurately diagnosed.

In view of the above, there exists the need to detect ciguatoxin contamination in a quantitative manner, to ensure that the toxin is detected even when it is present at very low levels. It is also desirable that such an assay be developed to quantitate the level of ciguatoxin in the blood of a patient so that the severity of the intoxication can be predicted. Furthermore, methods for quantitating the degree of contamination of fish or of the environment in which the fish live, and the subsequent prediction of the toxicity of fish coming from such areas, would be useful. Since currently-known extraction methods are very time-consuming, such assays would require the development of a method for rapidly and reproducibly extracting the toxin from the sample to be tested.

SUMMARY OF THE INVENTION

The present invention relates to methods for the rapid extraction of ciguatoxins from tissue samples, in order to allow rapid diagnosis of patients suspected of suffering from ciguatoxin poisoning or to enable rapid identification of the toxin in the tissue sample. One such method uses extraction into solvents, while another method employs binding the toxin to an immuno-affinity resin and subsequently eluting the toxin from the immuno-affinity resin.

The solvent extraction method comprises mixing a tissue sample with a first solvent to solubilize and extract ciguatoxin from the sample. A second solvent, which is not soluble in the first solvent and which extracts contaminants but not ciguatoxin, is then added. The phases formed by the first and second solvents are separated, and the first solvent phase is collected. The first solvent is evaporated from the first solvent phase to produce a residue which is resuspended in a third solvent. A fourth solvent, which is not soluble in the third solvent and which extracts contaminants but not ciguatoxin, is added to the third solvent/residue mixture. The phases formed by the third and fourth solvents are separated, and the third solvent phase, which comprises ciguatoxin, is collected. In a preferred embodiment, the first solvent comprises chloroform, the second solvent comprises methanol and water, the third solvent comprises 70% v/v methanol and 30% v/v acetonitrile, and the fourth solvent comprises hexane.

The immuno-affinity resin extraction method comprises applying a sample to a coupled antibody-resin, washing the coupled antibody-resin with a solution to remove unbound material, but not ciguatoxin, from the coupled antibody-resin, and then eluting ciguatoxin from the coupled antibody-resin. In a preferred embodiment, the coupled antibody-resin is washed with phosphate-buffered saline, and the ciguatoxin is eluted from the coupled antibody-resin with methanol.

DETAILED DESCRIPTION

The present invention relates to a method for quantitating ciguatoxin and for the rapid extraction of the toxin from contaminated tissues. Two methods are described herein, one of which employs extraction partitioning into organic solvents. The other method uses immuno-affinity chromatography.

RAPID EXTRACTION OF CIGUATOXIN

To extract ciguatoxin from a sample, the tissue or blood is preferably autoclaved. In the case of tissue, this makes the tissue softer and more easily broken up, to aid in the extraction process. In the case of blood, such as human blood, the sample is autoclaved to ensure that it does not contain any infectious agents. For each 1 to 2 gram(s) of autoclaved sample, about 2 ml of chloroform, or a first solvent, and about 4 ml of methanol are added, and the combination is mixed for about 1 min. to extract the toxins. The extraction process also results in the extraction of lipids and other chloroform- and methanol-soluble components. At the end of the initial extraction procedure, an additional volume of chloroform, about 2 ml, is added, and the combination is mixed for about 15 sec. At the end of the second extraction, about 2 ml distilled water is added, and the combination is mixed for about 15 sec. At the end of this third extraction, the combination is centrifuged at about 2,000 rpm for about 10 min., to separate the chloroform and the methanol/water, or second solvent, phases.

An upper methanol/water phase, an intermediate particulate phase, and a lower chloroform phase, all of which form upon centrifugation, are collected separately. Ciguatoxin, along with other lipids and lipid-soluble components from the sample, are extracted into the chloroform phase. The chloroform is evaporated under a stream of nitrogen, and the residue which remains is resuspended in about 1 ml of a mixture of about 70% v/v methanol and about 30% v/v acetonitrile, or a third solvent. To this mixture is added about 2 ml of hexane, or a fourth solvent, and the solution is mixed for about 15 sec. The methanol/acetonitrile and hexane phases are separated by centrifugation at about 2,000 rpm for about 10 min. Ciguatoxin is partitioned into the methanol/acetonitrile phase, and other components, some of which cross-react in the ciguatoxin assay, are partitioned into the hexane phase. The methanol/acetonitrile phase is collected and evaporated to dryness under a stream of nitrogen. The residue is then resuspended in PBS. The residue/PBS mixture is then assayed for the presence of ciguatoxin.

The rapid extraction method described above takes about 20 min. to complete—a considerably shorter amount of time than that required to extract ciguatoxin by using more conventional extraction techniques, such as that described below. Additionally, ciguatoxin prepared by this method does not contain materials which cross-react with the ciguatoxin assay method.

PREPARATION OF AN IMMUNO-AFFINITY MEDIUM

For the preparation of an immuno-affinity medium, antibodies are bound to a solid support material. Antibodies suitable for use in the present invention include monoclonal antibodies which react with antigenic determinants specific for a particular ciguatoxin species or combinations thereof, monoclonal antibodies which react with antigenic determinants common to all ciguatoxins or polyclonal antibodies against ciguatoxins, or anti-ciguatoxin antibodies. The terms "antibody against ciguatoxin" and "anti-ciguatoxin antibodies" as used herein mean an antibody which binds to the antigenic determinants of ciguatoxins and may include monoclonal or polyclonal antibodies. Such antibodies can be prepared by conventional techniques which are well known in the art. The animals used for the preparation of the antibodies are immunized with a ciguatoxin-containing fish extract (also referred to as "toxic fish extract") or a ciguatoxin analog. The preparation of such antibodies has been previously described in U.S. Pat. No. 4,816,392, incorporated herein by this reference.

The antibody is coupled to a solid support such as sepharose, which is commercially available from Pharmacia, Uppsala, Sweden, or other suitable solid-support medium. A convenient method for coupling the antibody to the solid support medium or resin is through protein A, derived form *Staphylooccus aureus*. Protein A interacts with the Fc portion of the IgG molecule to bind IgG from most mammalian species, as well as some other antibody classes. Since the interaction of protein A with IgG, for example, does not involve the immunoglobulin's antibody binding site, antibodies bound to protein A retain their ability to bind antigens. Such protein A coupled to a solid support medium, such as that sold by Pharmacia as Protein A-Sepharose CL-4B, is commercially available.

To prepare the antibody affinity medium, dry protein A-sepharose is hydrated in a buffer such as 0.2M sodium borate, adjusted to a pH of about 9.0, or other suitable buffer. After the hydration is complete, anti-ciguatoxin antibody is added to the protein A-sepharose. To form antibody resin, about 2 mg of anti-ciguatoxin antibody are added for about each ml of hydrated protein A-sepharose. The antibody-resin is incubated at room temperature for about hr., with continuous gentle rocking to allow the antibody to bind to the protein A. At the end of the incubation, the antibody-resin is washed at least twice with a buffer such as 0.2M sodium borate, adjusted to a pH of about 9.0, to remove any unbound protein from the antibody-resin. The washing process may be performed conveniently by resuspending the antibody-resin in a about 10 volumes of a buffer such as 0.2M sodium borate, adjusted to a pH of about 9.0, and collecting the resin by centrifugation at about $3,000 \times g$ for about 5 min.

The antibody so bound to the resin is not covalently bound and therefore may be leached from the resin during use. To prevent leaching, it is desirable to covalently couple the antibody to the protein A. Such coupling may be achieved by incubating the antibody-resin with a coupling agent such as dimethylpimelimidate. Coupling is performed by adding the coupling agent to the antibody-resin to a final concentration of about 20 mM. The pH of the reaction is adjusted to about 8.3 to promote the coupling reaction. The solution is incubated for about 30 min., at room temperature with constant agitation, to form a coupled antibody-resin. At the end of incubation, the coupling reaction is stopped by washing the coupled antibody-resin with a buffer such as 0.2M ethanolamine, as previously described. The coupled antibody-resin is resuspended in 137 mM NaCl, 1.6 mM KCl, 8.1 mM $Na_2HPO_4$, and 1.5 mM $KH_2PO_4$ (PBS) and stored at about 4° C. until required for use. If the coupled antibody-resin is to be stored for an extended period of time, it is desirable to add a preservative, such as about 0.01% merthiolate or other suitable preservative, to prevent bacterial or fungal growth in the coupled antibody-resin.

To determine the amount of antibody bound and coupled to the protein A-sepharose, aliquots are collected, during the preparation of the coupled antibody-resin, from the washed antibody-resin and the washed coupled antibody-resin steps. These samples are denatured in about an equal volume of a mixture comprising 62.5 mM Tris, pH 6.8, 2% SDS, 10% glycerol, 0.001% bromophenol blue, and 0.1M 2-mercaptoethanol by incubating the combination for 5 min at 100° C. The denaturation process denatures protein A and the antibody, and, in the antibody-resin sample, the two proteins can then be separated from each other, with the protein A remaining bound to the sepharose. However, in the coupled sample, the antibody and the protein A are covalently bound to each other and, upon denaturation, remain bound to each other and to the sepharose resin. After denaturation, the samples are subject to SDS polyacrylamide gel electrophoresis, as described by Weber and Osborn (*J. Biol. Chem.*, 244, 4406 (1969)) and modified by Laemmli (*Nature*, 277, 680 (1970)), both of which are incorporated herein by this reference. Preferably, the gels are about 10% w/v polyacrylamide gels.

After electrophoresis, the SDS polyacrylamide gels are stained with Coomassie blue. Successful binding of the antibody to the protein A-sepharose is observed by large amounts of stained material which co-migrate with antibody heavy chain, about 55,000 molecular weight, in aliquots collected before the coupling reaction. Little or no such bond is observed in the aliquot collected after the coupling reaction when the coupling reaction has been successful.

ISOLATION OF CIGUATOXIN ON IMMUNO-AFFINITY MEDIUM

The coupled antibody-resin prepared as described above is preferably packed into a column for use, although the coupled antibody-resin can also be used in a batchwise separation process.

Preferably, the coupled antibody-resin is packed into a 1 cc hypodermic syringe or other suitably-sized column. The coupled antibody-resin is washed with about 20 bed volumes of PBS.

Samples to be analyzed are then applied to the coupled antibody-resin, and the effluent is collected. The effluent is then reapplied to the coupled antibody-resin, and the effluent is again collected. This process may be repeated for a total of three or more times to ensure that all the ciguatoxin material present in the sample is bound to the coupled antibody-resin. After the ciguatoxin is bound to the coupled antibody-resin, any unbound material is washed from the coupled antibody resin with about 20 bed volumes of PBS. To elute the bound ciguatoxin, the coupled antibody-resin is washed with 100% methanol.

The coupled antibody-resin purification method allows the binding of large amounts of ciguatoxin to the coupled antibody-resin. Therefore, if the concentration of ciguatoxin is low, large, known volumes of the serum can be applied to the coupled antibody-resin. A ciguatoxin concentrate is then eluted in a small, known volume of methanol, which can be assayed for ciguatoxin. If the concentration of ciguatoxin is high, smaller, known volumes of the serum can be applied to the coupled antibody-resin to achieve a cuguatoxin sample which can be assayed. Thus, the use of the coupled antibody-resin allows the detection of ciguatoxin in samples, such as serum, even when it is present at very low, as well as high, concentrations.

CONVENTIONAL PREPARATION METHOD FOR EXTRACTS

Extracts, from either toxic or non-toxic frozen fish or other tissues, are prepared by weighing out about 250 g of tissue. The tissue may be autoclaved for about 10 min., if desired, to facilitate de-boning, to aid in the preparation of the extract, and to sterilize the tissue sample. The tissue is homogenized in a blender at high speed for about 10 min. The homogenized tissue is diluted 50% w/v with acetone, and the mixture is blended for about another 5 min. The mixture is then centrifuged at about 2,000 rpm for about 15 min., at 4° C., to separate the phases. The upper, acetone phase is decanted and collected, and the acetone extraction procedure is repeated, on the residue/aqueous phase, three more times. The extract is stored at about $-18°$ C. for about 10 to about 20 hrs. The solution is filtered in a cold Buchner funnel, and any residue is discarded. Acetone is removed from the non-volatile material by rotary evaporation.

Two volumes of methanol are added to the non-volatile material remaining after rotary evaporation, and the solution is mixed. The mixture is extracted three times with about a ⅓ volume of hexane. The hexane phase is separated from the methanol-containing phase and discarded. The methanol is separated from the non-volatile material by rotary evaporation.

An approximately-equal volume of chloroform is added to the non-volatile material, and the mixture is shaken to extract the non-volatile material. The chloroform phase is then collected. The chloroform extraction is repeated two more times, then the chloroform extracts are combined, and the chloroform is evaporated in a steam bath. The residue remaining after the chloroform is evaporated as crude extract.

Crude extract may be further purified by thin-layer chromatography (TLC) on silica gel TLC plates or by column chromatography.

The thin-layer chromatographic plate is developed with a chloroform/methanol mixture at a ratio of 8:2. The ciguatoxin fraction is recovered from the TLC plate, after the TLC plate has been run to separate the components of the crude extract, by scraping into a container the TLC medium from the section of the TLC plate containing the polyether fraction. The purified extract is then eluted from the collected TLC medium with chloroform:methanol in a ratio of 95:5. The eluate is evaporated to dryness and resuspended in about 5% Tween 60.

When column chromatography is used for the further purification of the crude extract, silicic acid, supplied by Mallicrodt, is used as the chromatography medium. Preferably, 100 mesh silicic acid is used, and it is activated at 100° C. for 1 hr., prior to use. The silicic acid is poured into a column of about 2 cm by about 5 cm, for use. The chromatographic medium is prepared by adding about a 1 cm layer of anhydrous $Na_2SO_4$ on top of the chromatographic medium in the column and equilibrating the chromatographic medium with chloroform. The crude extract is dissolved in chloroform to a concentration of about 40 mg/ml and applied to the chromatographic medium. The chromatographic medium is washed with about 20 ml of chloroform to elute triglycerides, fatty acids, cholesterol, and other non-polar compounds from the chromatographic medium. Ciguatoxins and other polyethers are eluted with a mixture of chloroform and methanol in a ratio of 95:5. The eluate is evaporated to dryness and resuspended in about 5% Tween 60.

CIGUATOXIN ASSAY METHODS

Methods for assaying ciguatoxins in fish, such as that described in U.S. Pat. No. 4,816,392, have used sticks coated with correction fluid to adsorb ciguatoxin from the flesh of contaminated fish. A sample of the ciguatoxin that may be present in the fish is adsorbed onto the correction fluid on the stick by inserting the stick into and contacting it with the flesh of the fish. The ciguatoxin adsorbed onto the correction fluid is then bound to an antibody against ciguatoxin, the antibody having previously been coupled to horseradish peroxidase. The presence of ciguatoxin is determined by assaying for the horseradish peroxidase activity.

Other assay procedures use "immunobeads," which comprise colored latex beads coated with antibody against ciguatoxin. Suitable immunobeads are made from blue-colored latex beads of about 0.3 to about 0.4 $\mu$m in diameter, such as those supplied by Seradyn, Inc., Particle Technology Division Ind., of Indianapolis, Ind. However, other-sized latex beads may be used.

Fish are screened by binding ciguatoxin to a test support. Suitable supports may be bamboo sticks, which are coated with an organic-base solvent correction fluid such as LIQUID PAPER, supplied by Pentel of America, Ltd., Torrance, Calif., to form paddle supports or membrane supports. Membrane supports comprise membrane material, such as that supplied by Millipore, of Bedford, Mass., under the name "MILLIPORE IMMOBILON-P MEMBRANE #IPVH," attached to a "dipstick." Polystyrene strips are suitable for use as dipsticks. The membranes are attached to the dipsticks by using an adhesive, such as "3M MEDICAL GRADE ADHESIVE #3044," or other suitable means of attachment.

After the support has been contacted with the fish tissue or extracts, it is contacted with the immunobeads. If ciguatoxin is present in the fish, the antibodies bind to the ciguatoxin on the support. Since the antibodies are also bound to the colored latex beads, the colored latex beads become bound to the ciguatoxin on the support. Therefore, a positive result, indicating the presence of ciguatoxin in the fish tissue, is observed by a change in color of the support due to colored latex beads being bound to the support.

When the antibody-horseradish peroxidase assay method is used, a positive result is observed by the accumulation of product from the enzyme assay.

In use, the assay reactions described above are compared to negative and positive controls. Negative controls are test supports which have not been exposed to ciguatoxins or their analogs. Positive controls are test supports which have been exposed to known concentrations of extract from a ciguatoxin-contaminated fish or to a ciguatoxin analog such as okadaic acid.

EXAMPLE 1

Assay of Toxic Fish Extract Using an Immunobead Assay

Membrane supports were exposed to various concentrations of a fish extract derived from toxic Po'ou fish (Wrasse fish). The membrane portion of a membrane support was inserted into solutions which contained either 1, 5, 10, or 25 mg/ml of fish extract. The membrane supports were removed and air-dried for about 5 min. or until the membranes were dry.

The membrane supports were fixed by immersing the membranes in absolute methanol for about 1 second. The membrane supports were again air-dried for about 5 min. Each of the membrane supports was then immersed in 0.5 ml of an immunobead suspension and allowed to remain in the immunobead suspension, undisturbed, for about 5 min. After 5 min., the membrane supports were removed from the immunobead suspension and washed three times with phosphate-buffered saline (PBS). Any excess liquid was removed by blotting the support with a paper towel.

The color developed on the test membrane supports was evaluated and the results scored.

The color intensity increased with increased concentration of extract.

EXAMPLE 2

Preparation of an Immuno-Affinity Medium

Sixty mg of dry protein A-sepharose (supplied by Pharmacia of Uppsala, Sweden) was mixed with 3.0 ml of 0.2M sodium borate, pH 9.0, and allowed to swell. 0.4 mg of anti-ciguatoxin monoclonal antibody, prepared as described in Example 1, was added for each ml of wet bed of protein A-sepharose. In this case, 2 mg of anti-ciguatoxin monoclonal antibody were added to form an antibody-resin. The antibody-resin was incubated at room temperature for hr., with continuous gentle rocking. At the end of the incubation, the antibody-resin was washed twice by resuspending the antibody-resin in 10 bed volumes of 0.2M sodium borate, pH 9.0, and collecting the antibody-resin by centrifugation at 3,000 g×5 min. The washed antibody-resin was resuspended in 10 bed volumes of 0.2M sodium borate, pH 9.0, and a 10 μl aliquot of the antibody-resin was removed.

Coupling reagent, dimethyl-pimelimidate, was added to a final concentration of 20 mM, and the pH was adjusted to above 8.3. The solution was incubated for 30 min. at room temperature, with constant agitation, to form a coupled antibody-resin. A 10 μl aliquot of the mixture was removed. After the incubation, the coupling reaction was stopped by washing the coupled antibody-resin once in 0.2M ethanolamine, as previously described. The coupled antibody-resin was resuspend in PBS.

EXAMPLE 3

Determination of the Efficiency of Coupling the Antibody to the Resin

Aliquots collected during the preparation of the affinity medium were analyzed by SDS gel electrophoresis. The assay relies on the fact that non-coupled monoclonal antibodies will be readily denatured and detected as a fraction that will migrate into the gel.

10 μl of 62.5 mM Tris, pH 6.8, 2% SDS, 10% glycerol, 0.001% bromophenol blue, and 0.1M 2-mercaptoethanol were added to the aliquots, and the samples were denatured by incubating for 5 min. at 100° C. 1 μl and 9 μl of the denatured samples were subjected to electrophoresis on a 10% SDS-polyacrylamide gel, prepared as described by Weber and Osborn (*J. Biol. Chem.*, 244), supra, and modified by Laemmli (*Nature*, 277), supra.

After electrophoresis, the SDS polyacrylamide gel was stained with Coomassie blue. Successful coupling of the antibody to the resin was observed by large amounts of stained material that co-migrated with antibody heavy chain, 55,000 molecular weight, in the aliquot collected before coupling and little or no such bond in the aliquot collected after the coupling reaction.

EXAMPLE 4

Isolation of Ciguatoxin Using an Immuno-Affinity Column

Coupled antibody-resin, prepared as described in Example 2, was packed into "1 cc hypodermic syringe columns" and washed with 20 bed volumes of PBS. Two ml of serum suspected of being contaminated with ciguatoxin was centrifuged at 100,000×g for 30 min. and the supernatant was collected. The supernatant was applied to the coupled antibody-resin, and the eluate was collected and reapplied. Again, the eluate was collected and reapplied to the coupled antibody-resin. Any unbound material was washed from the coupled antibody-resin with 20 bed volumes of PBS. The eluate was collected.

The coupled antibody-resin was then washed with 10 bed volumes of 0.1M phosphate buffer, pH 6.8. Material bound to the coupled antibody-resin was then eluted with 0.5 bed volumes of 100 mM glycine, pH 2.5. The eluate was collected and brought to neutral pH by the addition of 1/20 bed volume of 0.1M buffer phosphate, pH 7.7.

The eluates collected from the coupled antibody-resin were assayed as described in Example 1. The results indicate that no ciguatoxin was eluted from the coupled antibody-resin.

EXAMPLE 5

Isolation of Ciguatoxin Using an Immuno-Affinity Column

The procedure described in Example 4 was repeated, except the coupled antibody-resin was eluted with, in turn: 2 ml PBS; 1 ml 0.1M phosphate, pH 6.8; 2 ml 100 mM glycine, pH 2.5; and 2 ml PBS. Each of the eluates was collected separately.

The eluates, plus a sample that had not been chromatographed on the antibody-resin, were then tested, in triplicate, for their ciguatoxin content as described in Example 1. None of the eluted samples was found to be positive. The results indicate that no ciguatoxin was eluted from the coupled antibody-resin.

EXAMPLE 6

Isolation of Ciguatoxin Using an Immuno-Affinity Column

The procedure described in Example 4 was repeated, except 100 μl of 1 μg/ml okadaic acid in methanol was evaporated under a stream of $N_2$, resuspended in 1 ml serum, and applied to the coupled antibody-resin. The affinity medium was washed with: 2 ml of PBS; 2 ml 0.1M phosphate buffer, pH 6.8; 4 times with 0.5 ml 100 mM glycine, pH 2.5; 2 ml PBS; 2 ml 30% v/v methanol; 2 ml 80% v/v methanol; and 2 ml 100% methanol. The samples were collected separately and assayed for ciguatoxin, as described in Example 1.

All the eluates were found to be negative, indicating that okadaic acid was not eluted from the coupled antibody-resin or that it was not eluted at a concentration which could be detected by the assay method.

EXAMPLE 7

Isolation of Ciguatoxin Using an Immuno-Affinity Column

The procedure described in Example 6 was repeated, except the affinity medium was eluted with 2 ml PBS, 1 ml 100% methanol, and 1 ml PBS. The eluates were collected separately and assayed as described in Example 1. The methanol eluate was found to be positive for ciguatoxin, and the PBS eluates were found to be negative.

EXAMPLE 8

Rapid Extraction of Ciguatoxin from Serum Samples

Ten serum samples, from patients suspected of ciguatoxin intoxication or chronic fatigue syndrome (in which ciguatoxin-reactive substances are produced) were sterilized by autoclaving. To 1.5 g of autoclaved serum were added: 2 ml chloroform and 4 ml methanol and then mixed for 1 min.; 2 ml chloroform and mixed for 15 sec.; and 2 ml distilled water and mixed for 15 sec. The mixture was then centrifuged at 2,000 for 10 min. The upper methanol phase, the intermediate particulate phase, and the lower chloroform phase were collected separately. Chloroform was evaporated from the chloroform phase under a stream of $N_2$, and the samples were resuspended in 1 ml methanol.

The samples were tested for ciguatoxin or ciguatoxin-reactive cross-reactive substances as described in Example 1. The results are presented in Table I.

TABLE I

| Serum Sample Type | Sample No. | Methanol Phase[1] | Chloroform Phase[1] |
|---|---|---|---|
| Chronic fatigue syndrome | 1 | 0 | 1 |
| | 2 | 0 | 2 |
| | 3 | 0 | 6 |
| | 4 | 0 | 4 |
| | 5 | 0 | 3 |
| Ciguatera intoxication | 6 | 0 | 1 |
| | 7 | 0 | 0 |
| | 8 | 0 | 5 |
| | 9 | 0 | 0 |
| | 10 | 0 | 4 |

[1]The results are expressed on an arbitrary scale on which 0 indicates that no reaction was observed, and 6 indicates that a strong reaction was observed.

The results indicate that ciguatoxin or ciguatoxin cross-reactive substances were extracted into the chloroform phase.

EXAMPLE 9

Rapid Extraction of Ciguatoxin from Serum Samples

The procedure of Example 8 was repeated, except the residue from the chloroform phase was resuspended in 1 ml of 80% v/v methanol/water and then mixed with 2 ml of hexane. The methanol and hexane phases were separated, and each was tested for ciguatoxin, as described in Example 1. The results are presented in Table II.

TABLE 2

| Sample | Methanol[1] | Hexane[1] |
|---|---|---|
| 1 | — | — |
| 3 | 3 | 0 |
| 6 | 2-3 | 1 |
| 7 | 1 | 1 |
| Fish extract 1 | 1 | 1 |
| Fish extract 2 | 1 | 2 |

[1]The results are expressed on an arbitrary scale on which 0 indicates that no reaction was observed, and 6 indicates that a strong reaction was observed.

The purpose of the inclusion of the hexane extraction was to remove all non-polar components from the residue from the chloroform phase. However, the results indicate that the ciguatoxin does not partition as expected.

EXAMPLE 10

Rapid Extraction of Ciguatoxin from Serum Samples

The procedure described in Example 9 was repeated, except various concentrations of methanol in water, i.e., 100% v/v; 99% v/v; 95% v/v; 90% v/v; and 80% v/v, were used. The results are presented in Table III.

TABLE III

| | | |
|---|---|---|
| 100% | methanol | 6 |
| | hexane | 5 |
| 99% | methanol | 4-3 |
| | hexane | 3-4 |
| 95% | methanol | 4 |
| | hexane | 0-1 |
| 90% | methanol | 1 |
| | hexane | 3 |
| 80% | methanol | 1 |
| | hexane | 0-1 |

The results indicate that ciguatoxin cross-reactive substances are contained in both the methanol/water and hexane phases.

EXAMPLE 11

Rapid Extraction of Ciguatoxin from Serum Samples

The procedure of Example 9 was repeated, except the residue from the chloroform phase was resuspended in 1 ml of methanol/acetonitrile or methanol/water mixture, as indicated in Table IV. Each of the samples was then partitioned into hexane. The results are shown in Table IV.

TABLE IV

| Toxic Extract | Non-toxic Extract | Solvent Composition $CH_3CN$ | $CH_3OH$ | $H_2O$ | Result[1] |
|---|---|---|---|---|---|
| + | | | 80 | 20 | 5 |
| | + | | 80 | 20 | 4 |
| | + | | 100 | | 3 |
| | + | 60 | 40 | | 6 |
| | + | 40 | 60 | | 6 |
| | + | 30 | 70 | | 2[2] |
| + | | 60 | 40 | | 6 |
| + | | 40 | 60 | | 6 |
| + | | 30 | 70 | | 6 |

[1]The results are expressed on an arbitrary scale on which 0 indicates that no reaction was observed, and 6 indicates that a strong reaction was observed.
[2]The background reading for this test was determined to be 2.

The results indicate that 70% methanol and 30% acetonitrile provide a negative result with non-toxic samples and a positive result with toxic samples, and are suitable to partition ciguatoxin away from cross-reactive substances.

The above description of exemplary embodiments for the removal of ciguatoxins from the blood of an animal are for illustrative purposes. Because of variations which will be apparent to those skilled in the art, the present invention is not intended to be limited to the particular embodiments described above. Also, the invention disclosed herein may be practiced in the absence of any element which is not specifically disclosed in the specification. The scope of the invention is defined by the following claims.

What is claimed:

1. A method for rapidly extracting ciguatoxins from tissue comprising:
    mixing a tissue sample with a first solvent to solubilize and extract ciguatoxin from the sample;
    adding to the sample first solvent mixture a second solvent which is not soluble in the first solvent and which extracts contaminants, but not ciguatoxin, from the first solvent;
    separating the phases formed by the first and second solvents;
    collecting the first solvent phase;
    evaporating the first solvent, of the first solvent phase, to dryness to produce a residue;
    resuspending the residue in a third solvent;
    adding a fourth solvent which is not soluble in the third solvent and which extracts contaminants, but not ciguatoxin, from the third solvent;
    separating the phases formed by the third and fourth solvents; and
    collecting the third solvent phase wherein the ciguatoxin included in the third solvent phase is sufficiently pure to allow assaying for the ciguatoxins.

2. A method as recited in claim 1 wherein the first solvent comprises chloroform.

3. A method as recited in claim 1 wherein the second solvent comprises methanol.

4. A method as recited in claim 3 wherein the second solvent further comprises water.

5. A method as recited in claim 1 wherein the third solvent comprises methanol.

6. A method as recited in claim 5 wherein the third solvent further comprises acetonitrile.

7. A method as recited in claim 1 wherein the third solvent comprises 70% v/v methanol and 30% v/v acetonitrile.

8. A method as recited in claim 1 wherein the fourth solvent comprises hexane.

9. A method for rapidly extracting ciguatoxins from tissue comprising:
    mixing a tissue sample with chloroform to solubilize and extract ciguatoxin from the sample;
    adding methanol/water to extract contaminants from the chloroform phase;
    separating the phases formed by the chloroform and methanol/water;
    collecting the chloroform phase;
    evaporating the chloroform to dryness to produce a residue;
    resuspending the residue in methanol/acrylonitrile;
    adding hexane to extract contaminants from the methanol/acrylonitrile phase;
    separating the phases formed by the methanol/acrylonitrile and hexane; and
    collecting the methanol/acrylonitrile phase.

10. A method as recited in claim 9 wherein the methanol is present at a concentration of 70% v/v and the acetonitrile is present at a concentration of 30% v/v.

11. A method for rapidly extracting ciguatoxins from tissue comprising:
    mixing a tissue sample with a water immiscible solvent to extract ciguatoxin from the sample and a water miscible solvent to extract contaminants, but not ciguatoxin, from the water immiscible solvent; and
    collecting the water immiscible solvent phase.

* * * * *